United States Patent [19]

Shepherd et al.

[11] Patent Number: 5,074,857
[45] Date of Patent: Dec. 24, 1991

[54] BOLUS FOR RELEASING A BIOLOGICALLY ACTIVE SUBSTANCE INTO A LIQUID ENVIRONMENT

[75] Inventors: Michael T. Shepherd; Rodney C. Baker; Peter H. Marsden, all of Berkhamsted, England

[73] Assignee: Coopers Animal Health Limited, Berkhamsted, England

[21] Appl. No.: 870,173

[22] Filed: Jun. 3, 1986

[30] Foreign Application Priority Data

Jun. 11, 1985 [GB] United Kingdom ............... 8514666

[51] Int. Cl.⁵ .................................................. A23K 1/18
[52] U.S. Cl. .................................. 604/891.1; 424/438
[58] Field of Search ............................. 604/890–892, 604/48, 57–60, 93, 131, 156, 270, 95, 50, 54; 424/422, 426, 438; 128/784

[56] References Cited

U.S. PATENT DOCUMENTS

| | | | |
|---|---|---|---|
| 2,517,513 | 8/1950 | Vaernet | 604/891 |
| 4,326,524 | 4/1982 | Drake, Jr. et al. | 604/891 |
| 4,402,693 | 9/1983 | Roseman et al. | 604/890 |
| 4,449,982 | 5/1984 | Gould, III | 604/891 |
| 4,578,263 | 3/1986 | Whitehead | 604/892 |
| 4,606,354 | 8/1986 | Jacob | 128/784 |
| 4,623,345 | 11/1986 | Laby | 604/93 |
| 4,642,230 | 2/1987 | Whitehead et al. | 604/890 |

FOREIGN PATENT DOCUMENTS

| | | |
|---|---|---|
| 1603970 | 12/1981 | Australia . |
| 0140632 | 2/1986 | European Pat. Off. . |
| 0097507 | 11/1986 | European Pat. Off. . |
| 2122086 | 1/1984 | United Kingdom ............... 604/890 |

*Primary Examiner*—C. Fred Rosenbaum
*Assistant Examiner*—Sharon Finkel
*Attorney, Agent, or Firm*—Donald Brown

[57] ABSTRACT

A bolus for releasing a biologically active substance into a liquid environment according to this invention comprising an elongate core, at least one end of which is frustoconical and a liquid impervious casing at one end and open at the other disposed about the core, the bolus being so constructed that, in use, the casing is progressively shed as the core retreats, thereby releasing the active substance at a rate which varies over at least one time period, the casing being so structured as to retain its integrity without disintegrating in the absence of any support provided by the core.

15 Claims, 8 Drawing Sheets

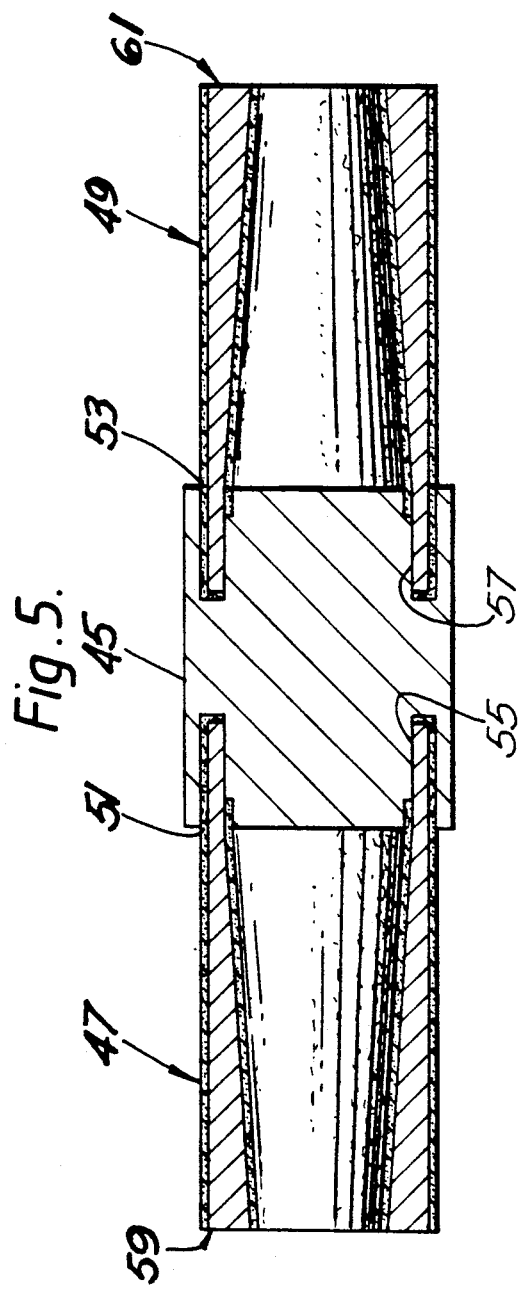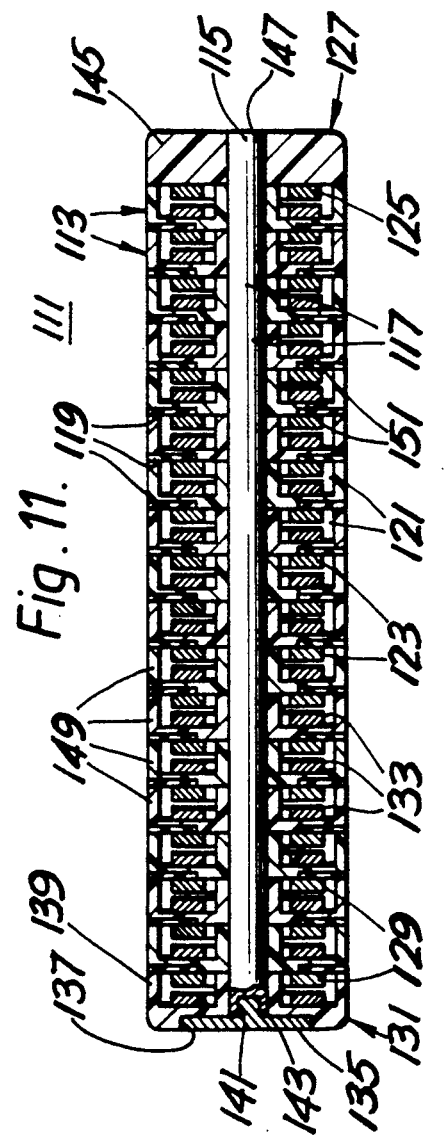

BOLUS FOR RELEASING A BIOLOGICALLY ACTIVE SUBSTANCE INTO A LIQUID ENVIRONMENT

FIELD OF THE INVENTION

The invention relates to improvements in a known type of bolus for releasing a biologically active substance into a liquid environment and of the kind comprising a generally elongate core surrounded by a liquid impermeable casing, the bolus having a construction such that in use, the casing has an opening at one or both ends of the core and is progressively shed as the core retreats, thereby releasing the active substance at a rate which varies over at least one time period.

This known type of bolus is normally used for administration of veterinary therapeutic agents, such as anthelmintics, or other substances, such as growth promotants, to ruminant animals, by releasing the agent in question into the rumeno-reticular sac. However, such a bolus also has applications outside the veterinary field, for example the administration of therapeutic or other agents to humans and the release of substances such as insecticides, aquatic herbicides or fish nutrients into rivers, lakes, reservoirs, tanks or pools.

BACKGROUND

One such bolus for intra-rumenal use is described in European Patent Specification No. EP 0 097 507 A. In this device, the core is a pellet of compressed particles, at least some of which comprise the active substance. The cross-sectional area of this pellet varies throughout its length and it is encased by a rigid skin of a brittle material, such as a synthetic resin adhesive, which requires the support of the core to maintain its integrity. As described, one or other end face of the device is cut to expose the core prior to administration to a ruminant. The rumen liquor is then said to act on the exposed face of the core to dissolve it and so release the active substance. It is intended that as the core dissolves, that part, and only that part, of the skin which thereby becomes unsupported, will no longer be able to maintain its integrity and so disintegrates. Thus, the device would release the active substance at either an increasing or decreasing rate according to whether the narrower or broader end face respectively is cut prior to administration.

In practice, it has been found difficult to realise a form of this particular known bolus which functions as intended. This may be due to difficulties in finding an optimum substance for the skin which will not become chipped or partially disintegrate in the rumen whilst the skin is still supported by the core. It could also in part be due to the physical characteristics of such compressed powder cores when coated in such a manner.

DESCRIPTION OF THE INVENTION

We have now found that these problems can be overcome by equipping the bolus with a casing which is (or at least some of its components are) sufficiently strong to retain integrity without disintegrating in the absence of any support provided by the core.

This provides, among other advantages, a more reliable and consistently reproducible release profile, that is to say that the variation of the rate of release of active substance more nearly corresponds to that intended. The manner in which the release profile may be adapted in accordance with different embodiments of the present invention will be described in more detail hereinbelow.

In a particularly preferred form of the bolus according to the invention, the casing along the length of the core comprises a tube of material degradable in the liquid environment, having a liquid impermeable brittle coating on its exterior surface. Functioning may be further optimised by the provision of a liquid impermeable brittle coating on the interior surface of the tube, or by the core containing a substance such that the abutment of the core and the interior surface of the tube provides a liquid impermeable seal. These measures ensure that the degradable material will only be subject to attack by the liquid environment at the open end or ends of the bolus where the casing has an opening.

Advantageously, any of the liquid impermeable coatings used in the aforementioned particularly preferred bolus form may be provided as a surface treatment of the tube or comprise epoxy resin. In the latter case, it may be necessary for the tube surface(s) to be pre-treated to ensure good bonding of the resin. The tube materials which render pre-treatment necessary and the techniques then to be employed will be readily apparent to those skilled in the art. It will be appreciated that as such tube coatings are brittle, they are not strong enough in themselves to maintain integrity without support of the bolus core. However, the present invention provides that sufficient strength is endowed to the coatings by the degradable tube which constitutes most or all of the remainder of the bolus casing. This contrasts with the prior art bolus referred to above where the integrity of the brittle coating is dependent on the support of the core itself. The degradable material of the tube may for example be a magnesium alloy and be in electrical contact with a member having a surface composed of a metal or alloy therof, more noble than magnesium, which surface is arranged so as in use to be in contact with the liquid environment. In this case the liquid of the environment will contact the exposed end face of the magnesium alloy tube and also the surface of the more noble metal and will act as an electrolyte, thereby promoting corrosion of the more reactive magnesium alloy. Conveniently, any surface treatment of this tube may be in the form of a surface anodising. Especially suited to the coating of such magensium alloy tubes is flame spraying with ceramic oxide, although this technique may also be used with such other tube materials as will be apparent to those skilled in the art.

Alternatively, the degradable material of the tube may be a soluble glass, preferably a water soluble glass. Ceramic flame spraying is also appropriate for the coating of soluble glass tubes. One suitable form of soluble glass is soluble sinter glass which is porous and comprises sintered glass fragments bonded together by heating. Another appropriate degradable material is biodegradable polymer, for example poly-$\beta$-hydroxybutyrate. In the latter case, any liquid impermeable coating may may also advantageously be a thin brittle layer of a non-biodegradable polymer.

In general, the material comprising the tube is degradable in the sense that it can be degraded when exposed to the liquid environment in which the bolus is placed during use. Such degradation may occur by one or more actions of the liquid, or a component thereof, on the material. Such actions include chemical reactions between the material and the liquid (i.e. by corrosion), the action of microorganisms such as bacteria (i.e. biodegradation), the dissolving of the material in the liquid, and also abrasion. It will be appreciated that the degradation of the material may be effected by the liquid or a component thereof on only one or some of the components thereof, this being sufficient to cause a breakdown of the tube structure.

The variation in release rate of the active substance may be of any desired form, for example an increase or a decrease in release rate over substantially the whole period the bolus is in use. The release rate may also be substantially constant over a part of the use period, either before, during or after an interval of increasing or decreasing release rate. In general, periods of increasing, decreasing and constant release rate may be provided for in a single bolus, according to the desired end result. Any or all of these periods may also be interspersed with one or more periods when no active substance (or one or more different active substances) is released, thus providing 'pulsed release'. Any increase or decrease in release rate may be linear or non-linear. The manner in which the bolus is constructed to achieve any of these release profiles will readily be apparent from the general and specific description hereinbelow, when regarded by one skilled in the art.

A particularly advantageous form of construction for administration of therapeutic agents or growth promotants to growing ruminant animals such as calves, provides an increasing release rate over all or a large part of the period the bolus is in use. This allows for the increasing dose required as body weight increases as the animal grows. In some cases it may be desirable to also provide for a period of constant release rate from the same bolus, to cater for a period during which the animal does not grow substantially.

In one preferred embodiment for providing an increasing release rate, at least one length of the core may be tapered to narrow in the direction of the open end or ends of the casing. This has the further advantage that at no time during use can the core fall out of the casing since it is geometrically retained by a corresponding narrowing taper on the interior wall of the casing.

For the avoidance of doubt, as used herein, the term 'tapered to narrow' refers to a surface profile which in cross section progressivly narrows in linear fashion as equally it alternatively refers to a surface profile which follows any sort of curve in cross section so as to provide the narrowing. Thus, to provide a constant increase in rate of release, the taper may be linear. Alternatively, to provide a variation in increase of rate of release, the taper may be curved.

Alternatively, the bolus may be arranged to release the required increasing amount of substance per unit time by providing the core with a concentration of the biologically active substance which decreases in the direction of the open end or ends of the casing.

Another way in which the bolus may provide an increasing release rate of substance is by the core being generally cylindrical and provided with a generally conical or frusto-conical insert, the broadest end of which is arranged at one of the open ends of the casing. Yet again, when the casing (as referred to above) comprises a tube of magnesium alloy in electrical contact with a member having a surface of a metal or alloy thereof, more noble than magnesium, then in use, the magnesium alloy may degrade by galvanic corrosion and the configuration be such that the corrosion current density increases over that period when the bolus releases an increasing amount of the substance per unit time. This may be achieved, for example, with a bolus wherein the cross-sectional area of the tube surface which is exposed to the environment, decreases during the period of use.

Any bolus according to the present invention may be arranged to release an immediate dose of biologically active substance upon being placed in the intended environment of use, this dose preferably being greater than a dose of active substance released immediately or soon thereafter.

The core of any bolus according to the present invention may be generally consolidated, that is to say it may comprise a single consolidated block containing the biologically active substance, although as indicated below, this may be divided into two portions. However, when the substance is one for combating infective organisms, for example parasites, whether in vivo or ex vivo, it may be desirable for the bolus to deliver the substance by pulsed release (vide supra), that is to say in a plurality of doses at space-apart time intervals. This is because with continuous release, if for any reason, the amount of substance released is insufficient to inactivate or kill all of the organisms, a resistance to the substance can be produced subsequent in generations. Pulsed release is particularly advantageous when it is desired to use the bolus for administration of anthelmintics to ruminants.

To provide such pulsed release, the bolus may be provided with a core comprising alternately arranged units of first and second kinds, the first kind containing a biologically active substance and the second kind containing either no, or a different biological active substance. Thus, the device can release a plurality of doses between which there is substantially none of the substance present in the liquid environment. Alternatively, in the period when substantially none of the substance is present, the device releases a second different biologically active substance.

In a pulsed release bolus according to the invention, there may be present, therefore, two biologically active substances, each in a respective kind of unit. However, the present invention extends to devices in which the core contains three or more biologically active substances. In the case of a continuous release device, these will be present in a core of the consolidated type, or with pulsed release devices, provided in the units of the first kind or distributed between units of both kinds For example, two different substances may be present in the first kind or distributed between units of both kinds. For of unit, with regard to the second aspect of the invention, the increase in release rate may be provided in respect of the amount of only one of the biologically active substances, in the amount of each of two or more (including all) of such substances, or in respect of the aggregate amount of two or more (including all) such substances.

In pulsed release devices according to the present invention where the casing is arranged so as in use to be open at both ends of the bolus, the units may be so arranged that in use, one or more biologically active components may be released alternately from each end. For example, initially, a first component may be released after a period of (say) 21 days from one end and then at the end of that period, a second biologically active substance may be released after a further period at 21 days from the other end, and so on alternately. Of course pulsed or continuous release of the same or one or more other biologically active component(s) may proceed simultaneously from both ends in this manner.

Particularly suited to pulsed release is a bolus according to the invention which is provided with a casing of the kind which comprises a plurality of peripheral segments, inert in the liquid environment of intended use. Prior art devices having such a casing are described in European Patent Specification No. EP 0 164 927 A. Such segments are not held together to form the casing in the absence of the core since they are held, e.g. by interference fit, on a central degradable rod, such as of a magnesium alloy, which forms part of the core. However, each as an individual component of the casing, has sufficient strength to maintain integrity and not disintegrate even when not so supported on the core. In the case of the present invention, the construction and manner of support of the segments may be as any described in the aforesaid European Patent Specification, for example the segments may be made of a suitable plastics material.

For intra-rumenal use, it is necessary for the bolus to be provided with a feature for preventing its regurgitation from the reticulo-rumenal sac. This feature may either comprise a suitable geometric configuration, for example, extending "wings" (as described in UK Patent Specfication No. 1 603 970) or appropriate weighting. One form of weighted bolus is that in which the casing is arranged so as in use to be open only at one end of the bolus and in which a weight is disposed at the end opposite thereto. Alternatively, to provide double the rate of release of the biologically active substance, the bolus may be provided with a casing arranged so as in use to be open at both ends of the bolus, a weight then being disposed mid-way along a length of the bolus and dividing the core into two portions. alternatively, a plurality of weights may be disposed at intervals along the length of the bolus.

In any event, where retention is provided by weighting, it is generally necessary for the bolus to have a total density in the range of from 2.25-3.5 g/ml, preferably about 2.5 g/ml and preferably, this density should increase as the bolus is progressively degraded. It will be appreciated that instead of by the discrete weights indicated above, it is also possible for the necessary weighting to be provided simply by virtue of the materials from which the bolus is made. However, this can result in regurgitation of the device after a certain amount of it has been degraded in the rumen, i.e. when its density has been reduced to below the minimum necessary to ensure its retention. Therefore, it is preferable that the bolus be provided with an additional weight.

A discrete weight may be made from any suitable material or combination of materials sufficient to achieve the overall required bolus density. For example the weight may be fabricated from a generally inert material such as iron, steel, copper, tin, lead, tungsten, zinc, chromium, cobalt, nickel or manganese, or an alloy of two or more such metals together, or an alloy of one or more such metals with one or more other metals. Particularly preferred is steel, iron or a zinc diecasting alloy. A weight of such inert metal would probably remain in the reticulo-rumenal sac after the rest of the bolus has degraded. Alternatively, a generally degradable material may be used, for example a degradable zinc alloy. The weight can also comprise a matrix of materials, for example shot of iron or another metal dispersed in an inert (e.g. polymer) or degradable (e.g. magnesium alloy) base material. Where the base material is inert, the weight will generally be retained in the rumenal sac whereas when the base material is degradable, after it has been degraded, the shot may be sufficiently small to be excreted.

Yet again, the weight may simply comprise a suitably dense granular material such as shot, held in a retaining sleeve, for example of a plastics material, or in a degradable shell, e.g. of magnesium alloy which itself is surrounded by a plastics or other inert sleeve. The granular material may also be dispersed within the core of the device.

Details of some preferred weights are given in the specific description.

For intra-rumenal use, a bolus according to the present invention will have weight and dimensions according to the particular ruminant animal for which it is intended. The particular weights and dimensions required in any given application will be apparent to those skilled in the art (for example having regard to the density requirements indicated above), but by way of example, a bolus for administration to cattle might have a length of from 30-200 mm, for example 50-150 mm, typically about 90 mm, a diameter of from 15-40 mm, for example 20-30 mm, typically about 25 mm. If intended for pulsed release, such a bolus might deliver 2-10 doses, typically 5 doses of biologically active substance(s) over a 1-12 month, for example 3-6 month, typically about 3½ month period, each dose comprising from 10 mg-10 g, for example 100 mg-1 g typically about 750 mg. The dependence of degradation of bovine intrarumenal boluses upon density and location in the reticulo-rumenal sac is described in J. L. Riner et al, Am. J. VetRes., 43, 2028-30.

The foregoing description of the present invention has mainly concerned intrarumenal applications. However, it will be appreciated that in general, the biologically active substance(s) contained in the core, is or are selected to have a desired effect in the environment in which the bolus is to be placed during use. These substances may be any of those referred to in European Patent Specification 0 164 927 A as referred to above. Amongst these, for administration to grazing animals, are trace elements, for example selected from magnesium, zinc, copper, cobalt and selenium. However, in the bolus according to the present invention, instead of, or in addition to being in the core, if they are provided in a form which is degradable in the intended liquid environment, such metals or their alloys may constitute the material of a degradable tube forming the bolus casing. Such trace elements may also be dispersed at appropriate concentrations in other media from which such a tube is fashioned, for example soluble glasses and bio-degradable polymers.

The active substance(s) in the core are also preferably formulated in like manner to that described in Specification EP 0 164 927 A. When the core contains two or more substances for simultaneous administration but which are incompatible when mixed in a single formulation, these may be provided in different formulations arranged in horizontal strata within the core (i.e. where the boundary between any two such strata is approximately parallel to the axis of symmetry and to the casing walls). Any of said strata may be provided with spaced apart doses to adminster one or more active substances in the form of pulsed release as hereinbefore described, any of said strata not containing spaced apart doses then serving to effect simultaneous continuous release.

DESCRIPTION OF THE DRAWINGS

The present invention will now be described in more detail by way of the following exemplary embodiments and with reference to the accompanying drawings in which:

FIG. 5 shows a longitudinal section through a bolus having a casing arranged so as in use to be open at both ends.

FIG. 11 shows in longitudinal section, a pulsed release bolus having individual peripheral segments.

FIGS. 1 and 2 show a bolus 1 comprising a tube 3 having a cylindrical exterior surface 5 and a frusto-conical interior surface 7 except at a rear end 9 where the interior surface is generally parallel to the exterior surface. The body 11 of the tube is formed of a magnesium alloy and carries a liquid impermeable coating 13, 15 on the exterior and interior surfaces respectively. However, the rear end of the tube is not coated on its interior or exterior surfaces. It should be noted that the end face 17 of the tube is also not coated. The coating may be of epoxy resin or the result of a suitable surface anodising treatment carried out on the magnesium alloy. In the case of epoxy resin coating, the magnesium is pretreated, either by pre-heating to 200° C. followed by cooling to room temperature, or by phosphate coating and in either instance, the epoxy is cured at 200° C.

Figure 1:
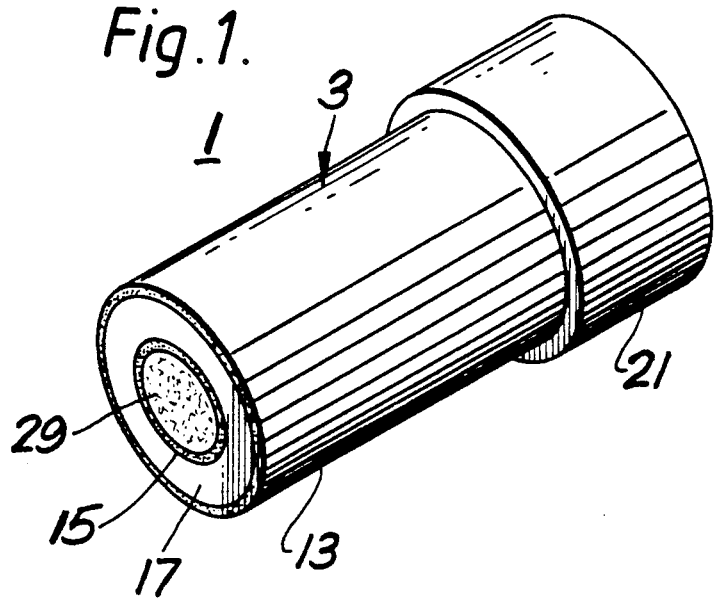
FIG. 1 shows in perspective view, a bolus according to the present invention.

The rear end of the tube is fixedly located by an interference fit in an annular slot 19 in cylindrical zinc alloy end weight 21. The surface coating extends a short distance into the slot at 23 to provide a liquid impermeable seal for the tube where it enters the endweight.

A core 25 contains an active agent consisting of growth promotant such as M 139603 or lasalocid, or an anthelmintic such as oxfendazole or levamisole, the active agent being dispersed in a suitable excipient with an appropriate binder such as will be apparent to those skilled in the art. The core is tapered so as to fit exactly into the cavity defined by the endweight and the interior surface of the tube. This arrangement also prevents the core from falling out. A convenient manner of manufacture is to prepare the core in a melted form which is then poured into the tube and allowed to set.

The endweight, tube and its surface coatings thus effectively constitute a liquid impermeable casing surrounding the core and open at the front end of the bolus.

The bolus is constructed by forming the tube, applying the surface coating and then inserting the core. The endweight is then fitted and the front end 27 of the bolus is faced off so that the end face of the tube and exposed surface 29 of the core lie in the same plane. This also ensures that the tube end face is free of surface coating.

In use, the bolus is administered to a calf by an oesophageal balling gun, after which it resides in the animal's rumeno-reticular sac. The exposed core surface is subject to attack by the rumenal fluids and begins to release the active agent. The core thereby starts to erode or dissolve so that the exposed surface retreats towards the endweight. At the same time, the end face of the tube and the endweight are also exposed to the rumenal fluid which acts as an electrolyte. The direct electrical contact between the tube and endweight sets-up a galvanic couple. Since magnesium is less noble than zinc, the magnesium alloy also begins to corrode in the rumenal fluid. As the tube progressively corrodes from the end face thereof, a portion of surface coating remains unsupported, but is sufficiently thin and brittle so as to fragment fairly quickly and thus break off, so that the coating does not extend beyond the tube end face. Moreover, the compositions of the core and magnesium alloy tube are chosen such that the exposed surface of the core and the end face of the tube retreat towards the endweight at generally the same rate, the two surfaces thus remaining more or less co-planar.

The casing along the length of the core, that is to say the tube with its coatings which are outside the endweight, progressively degrades only from the open front end. As degradation of the bolus progresses, the diameter of exposed core surface increases so that the amount of the active agent released per unit time also increases. The progressively decreasing area of exposed tube surface should also correspondingly increase the current density in the couple, this accelerating the rate of tube corrosion. This in turn should bring about an increase in active agent release rate. Of course alternatively, the diameter of the core and the wall thickness of the tube could be constant along their entire length and this aspect could instead be effected by providing an increasing concentration of the active agent in the core with increasing distance from the front end towards the endweight.

As well as administering the active agent to the animal, the bolus in use also releases magnesium, which although in a relatively small amount, would help towards combatting hypomagnesaemia.

When the core and tube have been degraded back to the endweight, the rear end of the tube embedded in the endweight dissolves and then over a longer period, so may the zinc alloy endweight. The endweight will either dissolve altogether, or when it becomes sufficiently small, be regurgitated or excreted. The net effect is therefore that when the bolus is spent, it might be that no fragments remain in the animal. It will be appreciated that the fragments of surface coating which have broken off are sufficiently small also simply to be excreted. Alternatively, the endweight may comprise a shell filled with iron shot to assist weight degradation at the end of the intended period of use.

Figure 2:
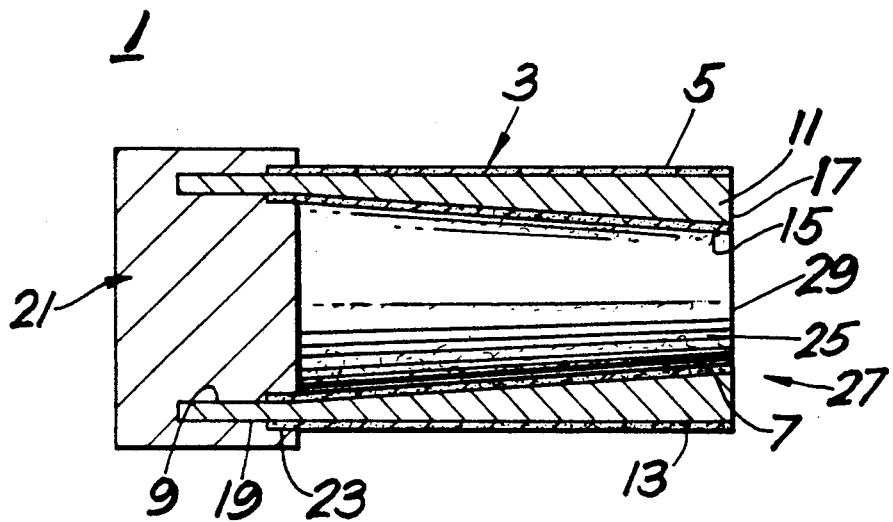
FIG. 2 shows a longitudinal section through the bolus shown in FIG. 1.
Figure 3:
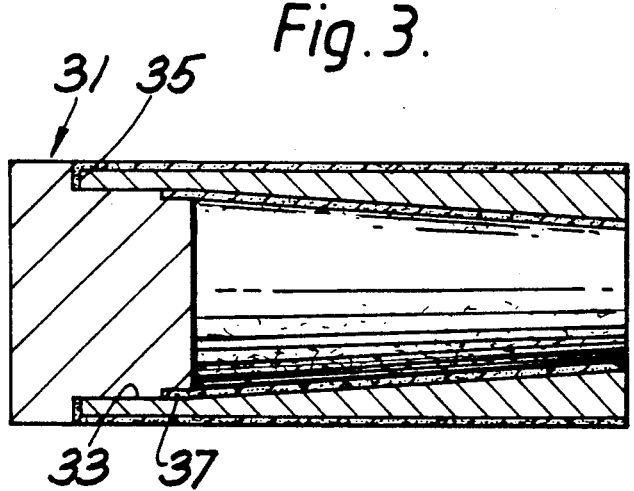
FIGS. 3 and 4 show in longitudinal section, variants of the bolus depicted in FIGS. 1 and 2.
Figure 4:
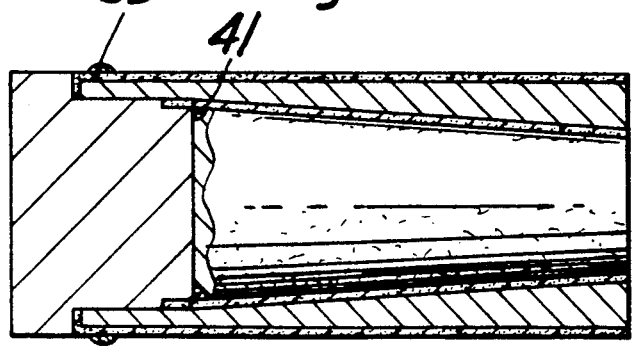

FIG. 3 illustrates a bolus constructed as that shown in FIGS. 1 and 2 except that the outer diameters of the tube with its surface coating and of the rear portion 31 of the endweight, are the same. In this case the rear end of the tube is fixed over a peripheral recess 33 in the endweight. The coating on the exterior surface of the endweight extends radially at 35 into the endweight for a length corresponding to the thickness of the tube rear end, and the coating on the interior surface also extends for a short distance at 37 into the annular recess, so providing a water impermeable seal at the interface between tube and endweight. This sealing may be enhanced by provision of additional annular seals 39, 41 of epoxy resin or other suitable material as shown in FIG. 4. Alternatively, the seals may comprise rings or washers of silicone rubber. In use, the boluses of FIGS. 3 and 4 function exactly as the bolus shown in FIGS. 1 and 2.

FIG. 5 shows a bolus in which a zinc alloy weight 45 is disposed midway along the length of the device joining two portions 47, 49, each identical to the coated tube in the bolus of FIG. 3. In this case however, instead of being fixed over a peripheral recess in the weight, the rear end of each tube is fixedly located by interference fit in respective annular slots 51, 53 at either end of the weight, in the manner shown for the bolus of FIGS. 1 and 2. This is to provide extra support in view of the additional length of the bolus. Regions 55, 57 on the interior surfaces at the rear ends of the tube are left uncoated to contact the material of the weight and so complete the required galvanic couple. This is an example of a bolus in which the casing (constituted by the weight and two coated tubes) is open at both ends 59, 61 of the bolus. In use, this device functions in a corresponding manner to those hereinbefore specifically described, except over any given time period, an increased amount (approximately twice) of active agent and magensium are released.

Figure 6:
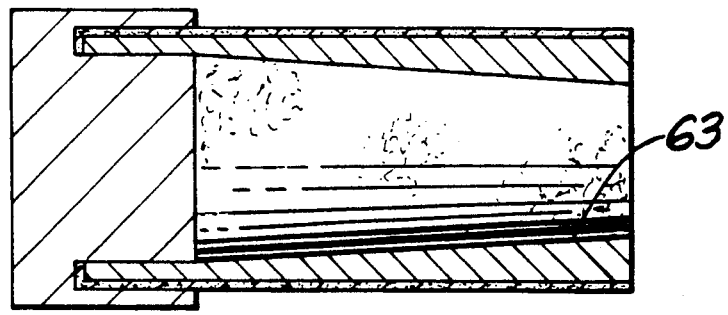
FIGS. 6 and 7 show in longitudinal section, further variants of the bolus depicted in FIGS. 1 and 2.

FIG. 6 shows a bolus in construction and operation, corresponding to that shown in FIG. 3, but with the single tube inserted in an annular slot as shown for the two equivalent tubes in the bolus of FIG. 5. Here though, the interior surface 63 of the tube remains uncoated, the tight seal fit between that surface and the core preventing ingress of liquid and so disrupting the operation of the device. In this case, to ensure exclusion of liquid, it may be necessary to include a water impermeable waxy substance in the excipients present in the core.

Figure 7:
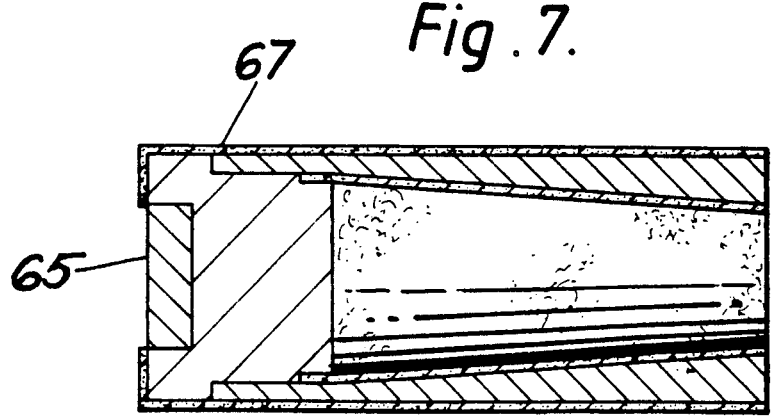

When it is desired to alter the rate of corrosion of the magnesium alloy tube, an insert 65 of a metal more noble than zinc, for example stainless steel, may be provided in the endweight of the bolus shown in FIG. 7. It is then necessary to extend the coating on the exterior of the tube over the outer surface 67 of the endweight except in the vicinity of the insert as shown. In use, when the core and magnesium alloy tube are spent, the zinc alloy weight will then corrode, parts of the coating on the exterior thereof being shed in small pieces, until there remains the insert with perhaps a remnant of the weight and its coating. When sufficiently small, this fragment will be regurgitated or excreted.

Figure 8:
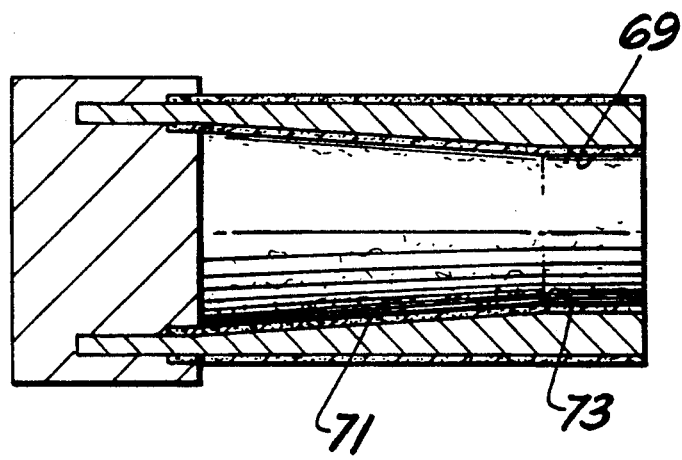
FIG. 8 shows a longitudinal section through a bolus providing an initial period of constant rate of release.

The bolus shown in FIG. 8 is equivalent in construction and operation to that described with reference to FIGS. 1 and 2 except that the interior surface of the tube has a region 69 at the front end of the device, which region has a constant internal diameter. The tube also has a region 71 where the internal diameter of the tube increases uniformally towards the endweight, the rate of increase in this region being greater than that for the bolus of FIGS. 1 and 2. This device may be administered to a calf and has a constant release rate for its initial period of use when the animal gains weight relatively slowly. When the bolus has eroded to a point 73 corresponding to the discontinuity in the internal diameter of the tube, the rate of release of active agent progressively increases to take account of the more rapid weight gain of the animal.

Figure 9:
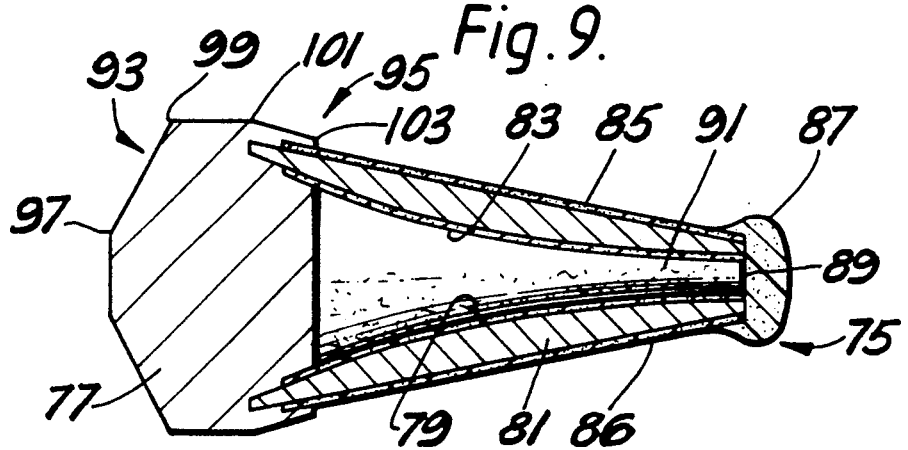
FIG. 9 shows a longitudinal section through a bolus providing a non-linearly increasing rate of release.

Of course the rate of total weight gain of animal per unit time may not be uniform at all and may for example increase throughout the normal growth period. In this case, a bolus may be used as shown in FIG. 9. The differences between this device and that shown in FIGS. 1 and 2 reside in that progressing from the front towards the endweight at the rear, the interior surface profile 79 of the tube 81 with interior and exterior coatings 83, 85 respectively, tapers in curved fashion. The outer surface 86 of the device is not cylindrical as with the device of FIGS. 1 and 2, but tapers towards the endweight to save on tube material. A wax nodule 87 is provided to protect the front face 89 of the device and to prevent release of active agent in the core 91 immediately on administration. It will be apparent that the casing (constituted by the coated tube and endweight) is not open at one end prior to use, but as described further hereinbelow, is arranged so as in use to be open. The endweight is radially cylindrical but the ends 93, 95 have stepped corners 97, 99, 101, 103 for streamlining and to aid administration. In terms of materials and construction, the device is otherwise the same as that depicted in FIGS. 1 and 2. After administration, the wax nodule is quickly eroded or melts, whereafter the device releases an increasing amount of active agent per unit time. The change in corrosion rate of the tube is complex since the exposed surface area will first progressively increase and after about the mid-point, decrease.

Figure 10:
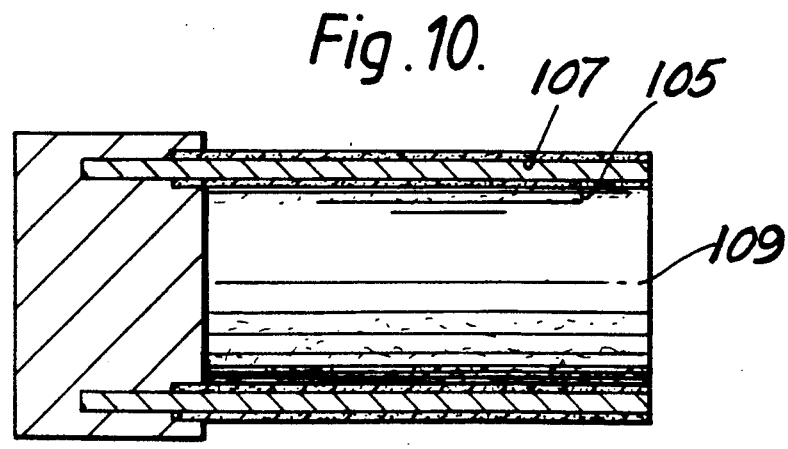
FIG. 10 shows in longitudinal section, a device having a cylindrical core.

The device illustrated in FIG. 10 is exactly the same as that of FIGS. 1 and 2 in terms of construction and operation, except that the interior surface 105 of the tube 107 has a constant internal diameter. The core 109 is uniformally cylindrical. In use, the device provides an increasing rate of release of the active agent since there is provided an increasing concentration of the active agent in the core with increasing distance from the front towards the endweight. Preferably the core is retained by a series of interlocking ribs and grooves (not shown) on the exterior circumference of the core and interior circumference of the tube, e.g. as described in European Patent Specification No. EP 0 025 699 A.

FIG. 11 illustrates a pulsed release device. A bolus 111 comprises a plurality of UPVC segments 113 mounted by interference fit on a central magnesium rod 115 passing through apertures in the centres of the segments. A seal is created between adjacent segments by silicone rubber washers 119. Respective annular cavities 121 are provided in each of the segments to have annular tablets 123 containing the active agent. The amount of active agent in each tablet increases progressively from the first tablet 125 at the front 127 to the last tablet 129 at the rear 131 of the device. The cavities also contain annular weights 133 of for example, compressed iron shot. At the rear, a stainless steel disc 135 is located in a recess 137 in the rearmost segment 139. The disc contacts the central magnesium alloy rod by means of cylindrical protrusion 141 fitted into corresponding hole 143 in the rod. At the front of the device, a blank UPVC segment 145 is also located by interference fit over the rod which extends through aperture 147 in the blank segment.

The outer portions 149, segments 113, washers 119 and disc 135 constitute the liquid impermeable casing of the device. The tablets 123 constitute a core containing a biologically active substance. In this case, the core is divided into portions by radially extending flange portions 151 of the segments 113 to enable pulsed release.

In use, when the device is administered to an animal, the galvanic couple between the stainless steel disc and magnesium alloy central rod promotes corrosion of the rod until the blank segment falls away and is eventually regurgitated. The first tablet 125 of the core is then exposed and released, together with its associated annular weight, the weight being sufficiently small to be excreted or regurgitated. Corrosion of the rod continues with successive shedding of segments and so release of tablets and weights. Increasing doses of active agent are released at generally regular intervals. The concentration of active substance in the rumen will fall in approximately linear fashion until a new tablet is released, whereupon the concentration will rise rapidly. Thus, a plot of concentration against time will have a 'sawtooth' form. Ideally, the amount of active substance in each tablet is tailored so that the maxima and minima lie between the amounts giving rise respectively, to the effective and toxic dose levels in the rumen, in terms of expected animal bodyweight. This is particularly desirable for administration of an anthelmintic such as oxfendazole or levamisole, or a growth promotant such as M 139603, to a calf. Desirably, the tablets are composed so that after release they provide a sustained delivery of substance. Thus, the concentration of substance in the rumen may decrease but not fall below the effective dose before release of the next tablet. The shed segments and washers, and the released weights will all be regurgitated or excreted, as finally will be the stainless steel disc. In an alternative embodiment, the bolus is as shown in FIG. 11 except that the volume concentration of the tablets is uniform. However, the overall volumes of the tablets, and hence cavities, increase from the first tablet 125 at the front end 127 to the last tablet 129 at the rear 131, so that in use the net effect is the same. In another alternative, the blank segment 145 may be replaced by a solid composition formulated to provide an initial dose of active substance.

Figure 12:
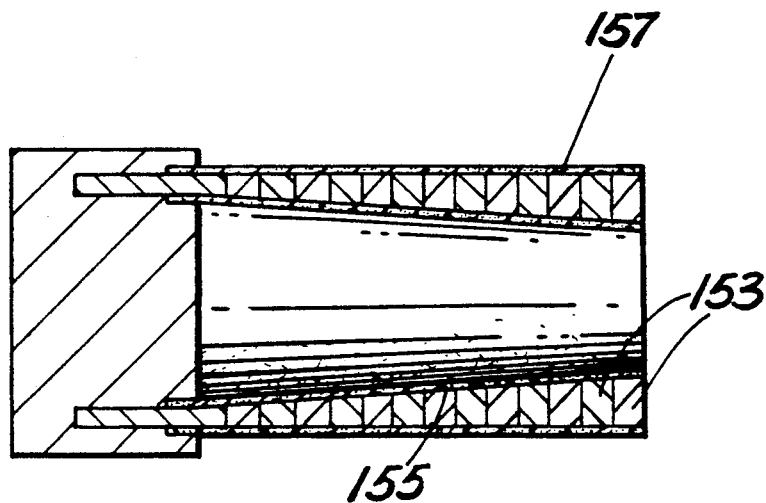
FIG. 12 shows a longitudinal section through a device in which the casing along the length of the core comprises a coated segmented tube.

To facilitate degradation, the tube in the bolus of FIGS. 1 and 2 may be segmented as shown in FIG. 12. The magnesium alloy tube is divided into a plurality of annular segments 153 supported by epoxy resin coatings on the interior 155 and exterior 153 tube surfaces. In use, degradation of this segmented tube tends to be accelerated because when a particular segment is nearly all corroded, the remnant may fall away with its associated coating portions.

Figure 13:
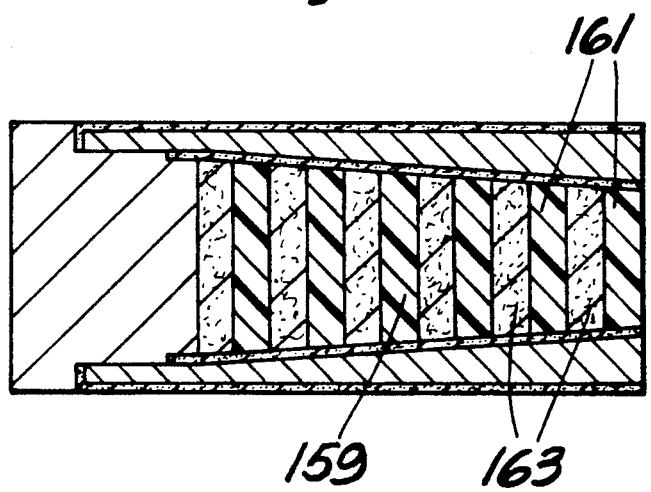
FIG. 13 shows in longitudinal section, a bolus as shown in FIG. 3 but adapted to provide pulsed release.

FIG. 13 shows a bolus identical to that of FIG. 3 in terms of operation and construction, except that the core 159 is divided into alternate segments or units, respectively comprising a non-biologically active substance 161 such as plaster of Paris and a composition 163 of an active agent, for example an anthelmintic such as oxfendazole or levamisole. It will be clear that this bolus provides pulsed release of the active agent into the rumen.

Figure 14:
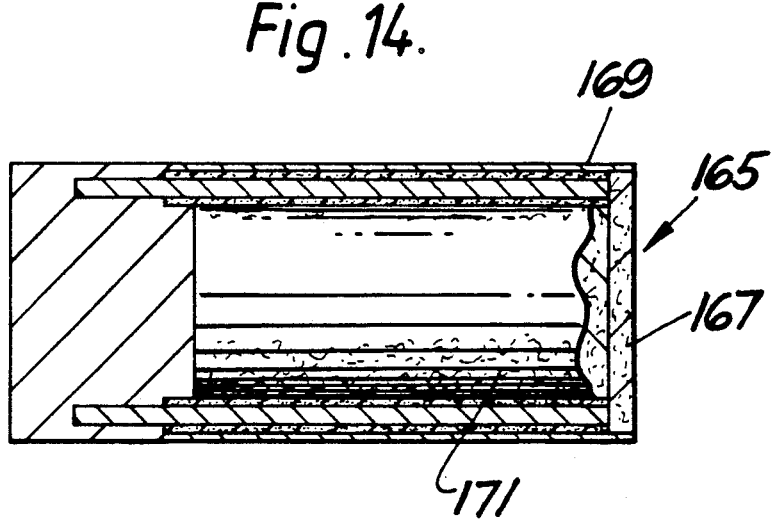
FIG. 14 shows in longitudinal section, a bolus as shown in FIG. 10 but adapted to provide an initial dose immediately upon administration.

FIG. 14 shows a bolus equivalent in construction to that shown in FIG. 10 except that the open end 165 is provided with a composition 167 of active substance to be released immediately upon administration. This is retained by a rolled tube 169 of cardboard or paper, the rolling being of helical configuration, conducive to the tube peeling away after being wetted by the rumenal fluids.

Thus, on administration, an immediate effective dose is released from the composition 167. Thereafter, a sustained dose of the same agent is released from composition 171 as with the bolus of FIG. 10. The dose released per unit time from composition 171 is less than the immediate dose released per unit time from composition 167.

Figure 15:
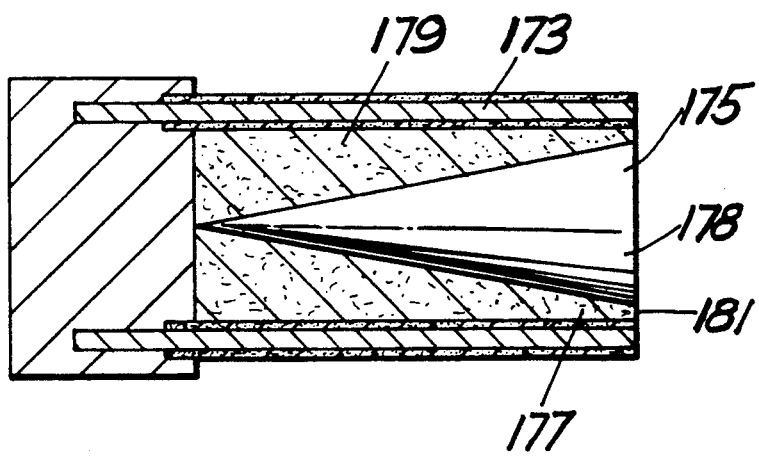
FIGS. 15 shows in longitudinal section, a bolus as shown in FIG. 2 but provided with a conical core insert.

The bolus shown in FIG. 15 is equivalent in construction and function to that shown in FIG. 2, except that the tube 173 has constant internal diameter as has the tube of the bolus shown in FIG. 10. In this case, the increasing dose release rate is due to provision of conical insert 175 in the core 177. The broadest end 178 of the insert is arranged at the open end of the casing. The insert is of a degradable material (e.g. a wax) but contains no biologically active substance. The insert is adapted to degrade in the rumen at substantially the same rate as the body 179 of the core which contains the active substance.

In use, as the bolus pogressively degrades, the area of the exposed surface 181 of the core body increases so releasing more active substance per unit time. Thus it will be appreciated that this device fulfils the requirements of both the first and the second aspects of the present invention.

In embodiments alternative to each of those described in FIGS. 1-15, in place of magnesium alloy, there is provided a water soluble glass, and in place of epoxy resin or surface anodised coatings, there is provided a coating of either epoxy resin or another liquid impermeable coating formed by surface sintering of the glass. The stainless steel insert of the device in FIG. 7 is then unnecessary and the endweight can be a simple cylinder of zinc alloy surrounded by a plastic coating overlapping for a short distance with the rear end of the tube. The stainless steel disc of the device in FIG. 11 may also be omitted, the rear segment then being without a recess and the magnesium alloy rod without a central hole at the rear.

Figure 16:
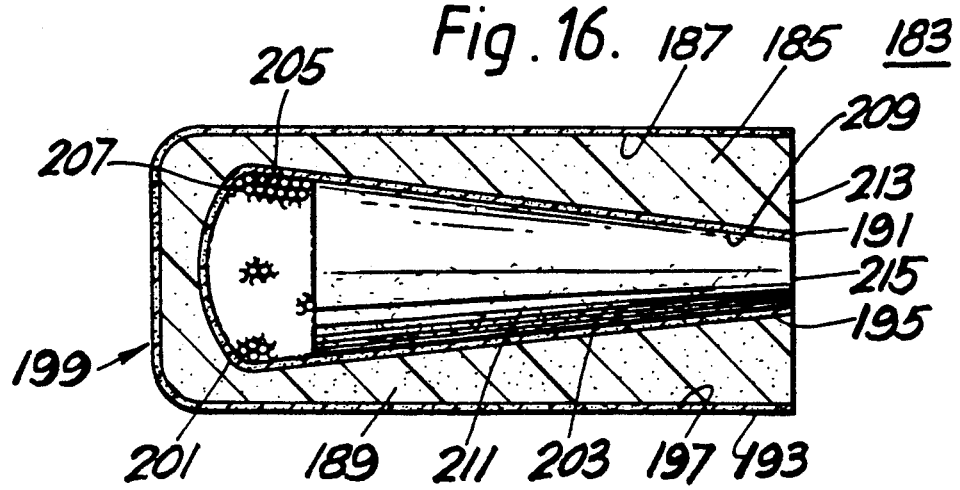
FIG. 16 shows a soluble glass bolus in longitudinal section.

FIG. 16 shows an intra-rumenal bolus 183 having a moulded water soluble shell 185. This provides a liquid impermeable casing 187, comprising a tube portion 189 having epoxy resin coatings 191, 193, respectively on its interior 195 and exterior 197 surfaces, and a rear portion 199 over which the epoxy resin coatings extend. The exterior surface 197 of the tube portion is cylindrical, and the interior surface 195 is frusto-conical and is contiguous with rounded interior surface 201 of the rear portion. The interior surface of the tube portion and rear portion of the casing define a cavity 203, the rear end 205 of which is filled with compacted iron shot 207. The remainder 209 of the cavity is filled with a core 211 containing an active agent of the kind specified above in respect of the bolus shown in FIG. 1. It should be noted that the end surface 213 of the tube portion is not covered with epoxy resin and that the narrow end 215 of the core is exposed.

After administration to a ruminant, in comparable fashion to devices hereinbefore described, the soluble glass tube and core degrade at substantially the same rate and the epoxy resin coatings become unsupported and flake-off. An increase in active agent release rate is provided by virtue the taper of the core. During use, the device is retained in the rumen because of the overall density provided by the iron shot. However, when all of the core has degraded, the shot falls out and will be regurgitated or excreted. The rear portion of the casing should then degrade to leave substantially no remnants in the animal.

Figure 17:
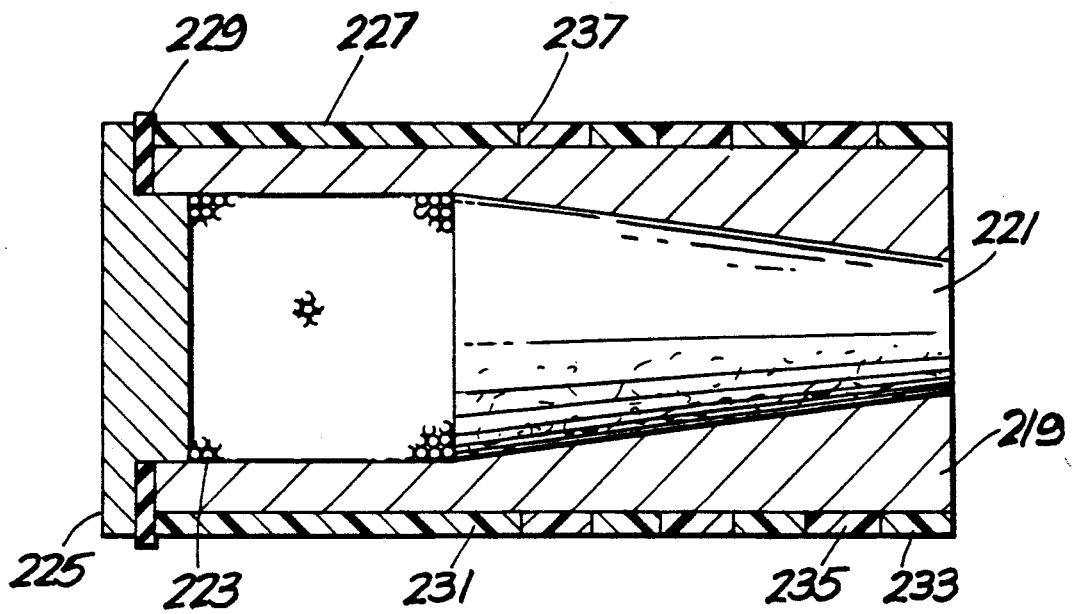
FIG. 17 shows in longitudinal section, an intrarumenal bolus having peripheral plastics segments.

The bolus 217 shown in FIG. 17 has a magnesium alloy tube 219 profiled as with the devices shown in FIGS. 1-7, and is similarly filled with a composition 221. Weight retention is provided by iron shot 223 which are expelled when the bolus is exhausted. Galvanic corrosion of the tube is controlled by mild steel endpiece 225. In this case, the outer surface of the magnesium alloy is protected from the rumenal fluids by plastics sheath 227 which is sealed against the endpiece by silicone rubber washer 229. As an alternative to this washer, to aid sealing, sheath 227 may be extended to partially cover the end piece. In any event, the sheath comprises a continuous portion 231 and discrete ring portions 233, 235 which abut the continuous portion at the end 237 remote from the end piece. The plastics material of the rings and of the continous portion are chosen so as when tightly fitted together over the tube by interference fit, a liquid-tight seal exists between them. Alternatively, sealing may be aided by the provision of silicone rubber washers (not shown) between the rings and between the rings and the continuous portion. In use, as the tube degrades in the rumen, the discrete ring portions are successively shed.

Figure 18:
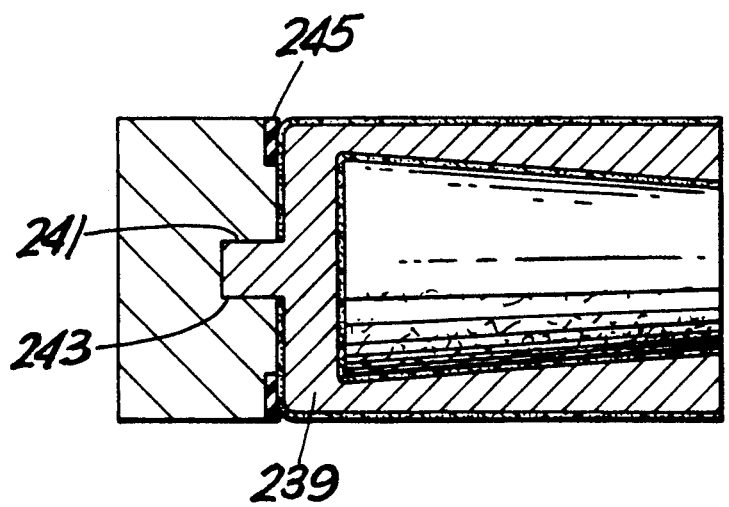
FIG. 18 shows in longitudinal section, an endweight mounting variant for the bolus in FIG. 3.

FIG. 18 shows an endweight mounting variant for the bolus shown in FIG. 3. The construction of this embodiment is exactly the same except that the core does not abut the endweight. Instead, the core terminates adjacent backing member 239 which extends into cylindrical lug 241, used to retain the endweight by interference fit in corresponding recess 243. Sealing is aided by silicone rubber washer 245.

Figure 19:
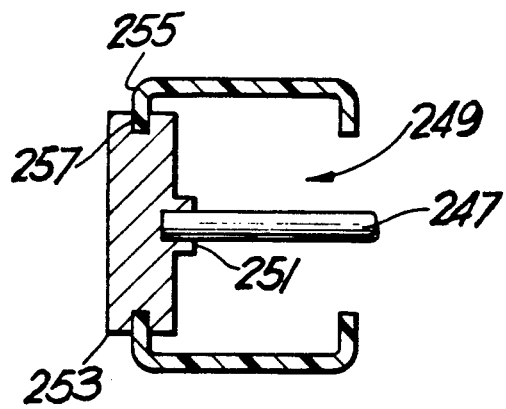
FIGS. 19-21 show alternative endweight shells.
Figure 20:
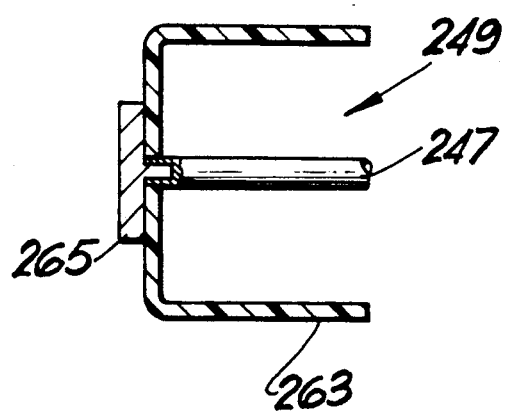
Figure 21:
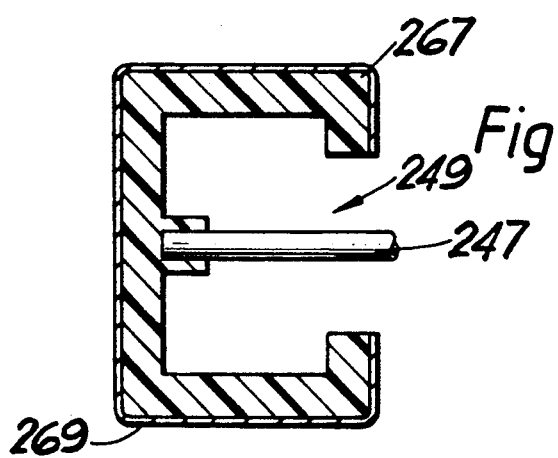

FIGS. 19-21 show preferred alternative endweight shells for a bolus such as that shown in FIG. 11. In each case the central magnesium alloy rod is denoted by the reference numeral 247. In all cases, the shell defines a cavity 249 for retaining loose weighting such as iron shot, to be expelled when the bolus is exhausted.

In FIG. 19, the rod is retained by interference fit in hole 251 in endpiece 253 of a metal more noble than magnesium. Annular lip 255 is injection moulded in situ to be retained in corresponding annular groove 257 in the periphery of the endpiece. FIG. 20 shows a construction wherein plastics shell wall 263 is retained on the magnesium alloy rod by interference fit. Interference fit also maintains contact between the rod and end-plate 265 of a more noble metal intended to promote galvanic corrosion of the rod. The plate also assists retention of the wall.

In FIG. 21, numeral 267 denotes a shell wall made from an electrically conducting polymer material. The rod is retained by interference fit in analogous fashion to the construction of FIG. 19. In this embodiment, galvanic corrosion of the rod is promoted by the provision of a nickel coating 269 on the exterior of the shell wall. Electrical contact between the rod and coating is maintained by the conducting property of the polymer from which the shell wall is fabricated. In a modified arrangement, the shell wall is made of a magnesium alloy and is integral with, or retained by interference fit on the magnesium alloy rod 247. The nickel coating is the same.

FORMULATIONS

In the following pharmaceutical formulations, the 'active ingredient' may for example be an anthelmintic such as oxfendazole or an growth promotant such as lasalocid or M 139603 (defined above).

The core of the devices shown in FIGS. 1-9, 12 and 15-18 may be formulated thus:

|  | Weight w/w |
| --- | --- |
| Active ingredient | 75.0% |
| Starch | 10.0% |
| PVP | 2.5% |
| Magnesium Stearate | 1.0% |
| Lactose | 11.5% |

The active ingredient, starch and lactose are blended then granulated with PVP solution in aqueous ethanol. The material is dried and mixed with the magnesium stearate lubricant and finally, the mixture is formed into a cylinder of about 100 mm length, diameter about 17 mm, the weight being 80 g.

For the device of FIG. 13, the mixture is compressed into a tablet formed in a conventional disc shape, weighing 1 g with a diameter of about 15 mm and a thickness of about 5 mm. For the device of FIG. 11, i.e. having a central rod, the weight of the tablet is 0.3 g and is annular shaped with a thickness of about 3 mm and a diameter of about 19 mm, with a central hole of about 12.25 mm diameter.

Compositions of active substance for other boluses specifically hereinbefore described are made in an analogous manner using techniques which will be apparent to those skilled in the art.

We claim:

1. A bolus for releasing a biologically active substance into a liquid environment comprising an elongate frustoconical core of biologically active substance and a liquid impermeable casing open at one end disposed about the core, said bolus being so constructed that, in use, the casing is progressively shed as the core retreats, thereby releasing the biologically active substance of the core at a rate which varies over at least one time period, characterized in that the casing is sufficiently strong to retain its integrity without disintegrating in the absence of any support provided by the core.

2. A bolus according to claim 1, further characterised in that the casing comprises a tube of material degradable in the liquid environment and having a liquid impermeable coating on its exterior surface.

3. A bolus according to claim 2, further characterised in that a liquid impermeable coating is also provided on the interior surface of the tube.

4. A bolus according to claim 2, further characterised in that abutment of the core and the interior surface of the tube provides a liquid impermeable seal.

5. A bolus according to any one of claims 2-4, further characterised in that at least one of the liquid impermeable coatings is a surface treatment of the tube.

6. A bolus according to any one of claims 2-4, further characterised in that at least one of the liquid impermeable coatings comprises an epoxy resin.

7. A bolus according to any one of claims 2-4, further characterised in that at least one of the liquid impermeable coatings comprises flame sprayed ceramic oxide.

8. A bolus according to any of claim 1, further characterised in that the core has a concentration of the biologically active substance which decreases in the direction of the open end or ends of the casing.

9. A bolus according to any of claims claim 1, further characterised in that the bolus is equipped with a feature for preventing its regurgitation from the reticulo-rumenal sac of a ruminant animal.

10. A bolus according to claim 1 further characterized in that the core comprises alternately arranged units of a first and second kind, the first kind containing a biologically active substance.

11. A bolus according to claim 1 further characterized in that the core comprises alternately arranged units of a first and second kind, the first kind containing a biologically active substance and the second containing a different biologically active substance, thereby to provide for pulsed release.

12. A bolus according to claim 1 further characterized in that the conical portion of the core is tapered in the direction of the open end of the casing.

13. A bolus according to claim 12, further characterised in that the taper is linear.

14. A bolus according to claim 12, further characterised in that the taper is curved.

15. A bolus according to claim 12, further characterised in that the core is provided with a non-tapered portion.

* * * * *